US005569189A

United States Patent [19]
Parsons

[11] Patent Number: 5,569,189
[45] Date of Patent: Oct. 29, 1996

[54] HYPODERMIC JET INJECTOR

[75] Inventor: James S. Parsons, Laguna Niguel, Calif.

[73] Assignee: Equidyne Systems, Inc., San Clemente, Calif.

[21] Appl. No.: 422,345

[22] Filed: Apr. 14, 1995

Related U.S. Application Data

[63] Continuation-in-part of Ser. No. 130,022, Sep. 29, 1993, Pat. No. 5,499,972, which is a continuation-in-part of Ser. No. 952,562, Sep. 28, 1992, abandoned.

[51] Int. Cl.⁶ .................................................. A61M 5/30
[52] U.S. Cl. .................................. 604/68; 604/72; 604/22
[58] Field of Search .............................. 604/68–72, 187, 604/218, 131, 133, 134, 135, 140, 141, 156, 157

[56] References Cited

U.S. PATENT DOCUMENTS

| | | |
|---|---|---|
| 2,398,544 | 4/1946 | Lockhart . |
| 2,737,946 | 3/1956 | Hein . |
| 2,762,369 | 9/1956 | Venditty . |
| 2,762,370 | 9/1956 | Venditty . |
| 2,800,903 | 7/1957 | Smoot . |
| 2,902,994 | 9/1959 | Scherer . |
| 3,335,722 | 8/1967 | Lowry et al. . |
| 3,688,765 | 9/1972 | Gasaway . |
| 3,788,315 | 1/1974 | Laurens . |
| 4,165,739 | 8/1979 | Doherty et al. . |
| 4,378,015 | 3/1983 | Wardlaw . |
| 4,518,385 | 5/1985 | Lindmayer et al. . |
| 4,643,721 | 2/1987 | Brunet . |
| 4,680,027 | 7/1987 | Parsons et al. ..................... 604/68 |
| 4,722,728 | 2/1988 | Dixon . |
| 4,874,367 | 10/1989 | Edwards ............................ 604/72 |
| 4,913,699 | 4/1990 | Parsons ............................. 604/68 |
| 5,024,656 | 6/1991 | Gasaway et al. . |
| 5,026,343 | 6/1991 | Holzer . |
| 5,062,830 | 11/1991 | Dunlap . |
| 5,085,641 | 2/1992 | Sarnoff et al. . |
| 5,190,523 | 3/1993 | Lindmayer . |

Primary Examiner—Randall L. Green
Assistant Examiner—V. Alexander
Attorney, Agent, or Firm—Christie, Parker & Hale, LLP

[57] ABSTRACT

A system is provided that is useful for a hypodermic jet injection of medication without piercing the skin with a needle. The system includes a spring actuated needleless hypodermic injector device for injecting medication through the skin. The injector device includes an ampule assembly having a chamber for holding liquid medication and an injector for receiving and mounting the ampule assembly. A plunger assembly, movable within the ampule chamber is used for drawing liquid medication into the ampule chamber and for ejecting liquid medication out from a chamber. The injector includes a spring actuated piston which provides a force to move the ampule assembly plunger and thereby force liquid medication to leave the chamber at such velocity that it can be hypodermically injected at an injection site. The system also includes a coupler for use on a medication vial for transferring medication to the ampule assembly. The system also includes a cocking/carrying case which automatically cocks an injector device when it is placed within the case, and the lid is closed.

7 Claims, 9 Drawing Sheets

HYPODERMIC JET INJECTOR

CROSS REFERENCE TO RELATED APPLICATION

This is a continuation-in-part of application Ser. No. 08/130,022 filed Sep. 29, 1993, entitled "HYPODERMIC JET INJECTOR," now U.S. Pat. No. 5,499,972 which is a continuation-in-part of application Ser. No. 07/952,562 filed Sep. 28, 1992, now abandoned, the entire disclosure of which is incorporated herein by reference.

FIELD OF THE INVENTION

This invention relates generally to needleless hypodermic drug delivery systems, and more particularly to spring actuated jet injection devices that avoid piercing the skin by utilizing a high pressure liquid stream to pass a medicament or other liquid through the skin.

BACKGROUND OF THE INVENTION

Jet injection devices administer intramuscular and subcutaneous medications without the use of needles. Among the many advantages of jet injection are the reduction of pain and apprehension associated with needles, the elimination of needle stick injuries and the reduction of environmental contamination associated with needle disposal. Jet injection devices are useful in a wide range of drug therapies including immunization vaccines, hormones and local anesthetics, as well as the administration of insulin to the diabetic population, where individuals may require a number of daily injections. Thus, their use has become of increasing interest, particularly by persons of limited physical ability such as the elderly, or the very young.

The principles of jet injection and the advantages of drug delivery systems over hypodermic needles have long been known. However, very few jet injection devices have achieved commercial success in the marketplace. This lack of acceptance by the user community can be attributed to a number of factors, chief among which are: the high cost of prior art injection devices, complex filling techniques, and mechanical designs which have potential to inflict serious injury if an injector device were inadvertently fired without a medicament container inplace.

One existing needleless injection device is described in U.S. Pat. No. 4,874,367 to Edwards. It employs a sealed ampule that is prefilled with a selected amount of medication. The prefilled ampule is attached to a separate spring-loaded firing mechanism which, when triggered, propels a ramrod out of the front of the mechanism and against a plunger located in the ampule. The ramrod drives the plunger against the medication, producing a high pressure jet for injection purposes. The plunger expels the medication from a discharge orifice into the patient's subcutaneous tissue.

Although effective in some respects, this prior art apparatus is severely limited in practical application. In order to cock the firing mechanism, the user is required to force the ramrod back into the firing mechanism by pushing the device against a solid surface such as a table top until the ramrod latches behind a trigger mechanism. Thus, the strength of an individual user places limits on the spring force that can be developed in the device. A spring force low enough to be practical for the elderly or the very young to cock is typically inadequate to produce reliable jet injection pressures for most adults. In addition, the firing mechanism, having a spring actuated ramrod, which extends outside of the device body, has the potential to inflict serious injury if inadvertently fired without the ampule in place. Consequently, it is desirable to have a needleless injection system that overcomes these concerns.

Moreover, the fixed dose ampule must be prefilled at the factory and then attached to the injector to be administered when required. In practice however, this procedure is not practical, for the simple reason that drug products cannot be stored in plastic containers for the long periods of time typically experienced by a factory prefilled ampule. The only approved material for long term liquid medication storage is type-I glass, which is used for virtually all drug products. However, due to the dynamics of jet injection in which the ampule is subjected to very high pressures during the injection stroke glass is not a suitable material for the ampule because it is easily shattered. Consequently, it is desirable to have a unit dose ampule which may be attached to a conventional glass container at the time of use and filled with an accurate dose of medication. The ampule must be made of a high strength plastic material.

U.S. Pat. No. 4,913,699, to Parsons, describes a needleless injection device having a firing mechanism that operates to release compressed gas from a storage compartment. The compressed gas acts upon a piston which drives a plunger that ejects a selected dosage of medication through an aperture in the discharge end of the device. However, the medication to be administered must first be drawn into a liquid medication containing chamber provided in the interior of the injector before being dispensed. Thus, although being self-cocking, reloadable, and reusable, the device is somewhat complicated. In addition, no provision is made for filling the medication chamber directly from standard medication containers. In order to fill the medication chamber, a complex liquid transfer system is required.

Injectable medications fall into two different categories; namely, unit dose drugs such as vaccines and analgesics and variable dose drugs such as insulin where the dose size must be adjusted to meet the immediate needs of the individual at the time of administration. When a variable dose is required, as in the case of the administration of insulin, a very accurate amount of medication must be transferred to a variable dose ampule. Insulin doses are typically marketed in 3 ml and 5 ml syringe cartridges, as well as provided in bulk in a standard 10 ml medication vial. These dose categories and differing medication source containers, therefore impose conflicting design requirements on ampules or syringe compartments provided in prior art jet injection systems.

U.S. Pat. No. 4,680,027 to Parsons, et al. describes a hypodermic injection apparatus which includes a disposable syringe which can be inserted into a power supply mechanism. The syringe has a cavity for holding liquid medication and an aperture on one end through which liquid medication can flow into and out of the cavity. The syringe has a hollow, tubular needle removably attached to it so that the syringe can be filled by inserting the needle into a container of liquid medication. Liquid is drawn from the container by pulling on a plunger disposed within the syringe cavity which causes a suction to draw liquid from the container and into the cavity in a conventional manner.

The power supply mechanism has a trigger which, when pulled, unseals a container of compressed gas to provide a motive force to force the syringe plunger toward the aperture so that the liquid medication is ejected through the aperture with sufficient force to penetrate the skin.

The above-described power supply mechanism includes safety interlocks, one of which prevents securing the syringe within the power supply mechanism until the needle is removed. A second interlock prevents movement of the trigger so that the gas container cannot be opened unless the syringe is fully secured in the power supply mechanism. Both interlocks are both relatively complex mechanical systems.

Consequently, there is a need for a needleless hypodermic injection device which has an enhanced simplicity of design, including a simple design of the interlock mechanisms. Furthermore, there is a need for a needleless hypodermic injection system which includes a medication ampule which may be rapidly and conveniently attached to a variety of medicament sources and which extracts accurate doses of medication therefrom without the risk of injury due to needle use or the contamination hazards attendant with needle disposal.

In this regard, it is desirable to have a convenient needleless jet injector device that is dimensioned and arranged to be grasped in the hand of a user. The system should comprise both a permanent injector firing mechanism and a disposable ampule cooperating in a novel design having simplicity in both structure and function. The disposable ampules should be such that the user can fill it with a selected dosage conveniently and accurately from existing medication vials. The injector firing mechanism should be conveniently and safely operated without the need for a user to force the apparatus against a piece of furniture in order to cock a spring.

SUMMARY OF THE INVENTION

This invention relates to a system for providing needleless hypodermic jet injection of medication. The system includes (1) a spring operated needleless hypodermic device of simple, efficient and reliable design for injecting variable doses of liquid medication (2) a coupling assembly for use on a standard medication vial for transferring medication to the injection device and (3) a cocking/carrying case for providing sufficient mechanical advantage for simple and efficient cocking of an injector device.

The spring actuated needleless hypodermic jet injection system includes an ampule assembly having a shell with a chamber for holding liquid medication and an injector for receiving and mounting the ampule assembly. The ampule assembly includes an orifice in the front end of the ampule shell through which liquid medication can be drawn into and ejected out of the chamber. A plunger assembly, movable within the chamber, is used for drawing liquid medication into the chamber and for ejecting liquid medication out from the chamber.

The injector provides a force to move the ampule assembly plunger to thereby force liquid medication to leave the chamber via the orifice at such a velocity that it can be hypodermically injected at an injection site. The injector includes a cylindrical housing defining a longitudinal channel, and has an open front end which is configured to received one end (the back end) of the ampule assembly to thereby externally mount the ampule assembly on the injector. A piston is mounted for sliding movement in the longitudinal channel and applies the force to the plunger assembly. The channel within the cylindrical housing is configured to house a spring, in communication with the piston, for accumulating and storing a sufficient amount of energy when compressed, that when released, drives the piston against the plunger assembly to produce sufficient to cause liquid medication to leave the ampule chamber via the orifice at such a velocity that it can be hypodermically injected at an injection site.

A trigger assembly is provided for manually releasing the spring and, thus, the stored energy to provide a force on the piston to thereby move the piston forward and into contact with the ampule assembly plunger.

An interlock safety assembly is also provided to prevent the release of the stored energy by the trigger assembly unless an ampule assembly is coupled to the injector. The interlock safety assembly is connected between the trigger assembly and coupling means provided in the open end of the injector housing and is operatively responsive to the ampule assemblies being coupled to the injector housing.

In a further embodiment the injection system includes a liquid transfer unit for use with a syringe cartridge for transferring medication to the ampule assembly which comprises a hollow tubular body with a threaded opening in a base end for receiving a jack screw. The jack screw communicates with the syringe cartridge to apply pressure to liquid within the cartridge when the jack screw is rotated. A transfer adapter is connected at an opposite end to the tubular body and includes a canula which extends into the tubular body and pierces the syringe cartridge.

Means are provided for coupling the transfer adapter to the orifice end of the ampule assembly so as to place the orifice of the ampule assembly in communication with the transfer adapter. As the jack screw is rotated, liquid medication is forced from the syringe cartridge and into the ampule assembly through the orifice.

In another preferred embodiment of the injection system provided in accordance with the invention, a vial coupler is provided for use on a standard medication vial for transferring medication to the injector. The vial coupler comprises a shroud cavity and a locking collar spaced apart from each other on opposite ends of the body. The shroud cavity is configured to receive the cap of a standard medication vial. The locking collar is configured to engage the orifice end of an ampule assembly.

A cannula extends through the center of the shroud cavity of the vial coupler and is positioned in the shroud cavity with the point extending a sufficient distance into the shroud cavity so that the self sealing membrane of a medication vial cap is pierced by the canula when the vial coupler is on the vial.

In a further embodiment of the hypodermic injection system the injector is received in a cavity provided to hold the injector in a cocking/carrying case. The cocking/carrying case comprises an elongated rectangular base and cover hingedly connected together along a short side such that the cover describes an arc when it is closed along the base. Means for cocking the injector are operatively responsive to the closing of the cover. The cocking means engage the injector in order to compress the spring to accumulate a suitable amount of energy.

In particular, the cocking/carrying case includes a shuttle which is mounted to slide along the base and which includes a centrally mounted and longitudinally extending ramrod. The ramrod is configured to extend into the open front end of the injector housing when the injector is placed in the cavity. The ramrod bears against the injector piston such that when the lid is closed the ramrod exerts a force on the piston to thereby compress the spring to accumulate the suitable amount of energy.

BRIEF DESCRIPTION OF THE DRAWINGS

The above-described and other features and advantages of the invention will be more fully understood when considered in connection with the following detailed description and accompanying drawings, wherein:

FIG. 8a is a semi-schematic cross-sectional side view of the cocking/carrying case of FIG. 7a.

DESCRIPTION OF THE INVENTION

This invention relates to a system for providing needleless hypodermic jet injection. The system components include a spring-actuated needleless hypodermic injection device, a medication ampule assembly a plurality of medication transfer devices for transferring medication from standard medication vials or drug and syringe cartridges to the medication ampule assembly, and a cocking/carrying case, equipped with an internal linkage that resets the spring to a cocked condition whenever the injection device is placed within the case and the lid of the case is closed.

Figure 1:
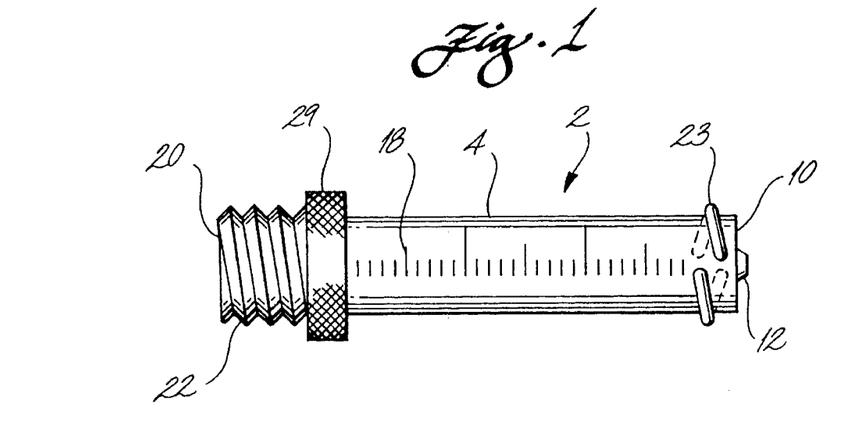
FIG. 1 is a semi-schematic plan view of a medication ampule provided in accordance with practice of principles of the invention.
Figure 2:
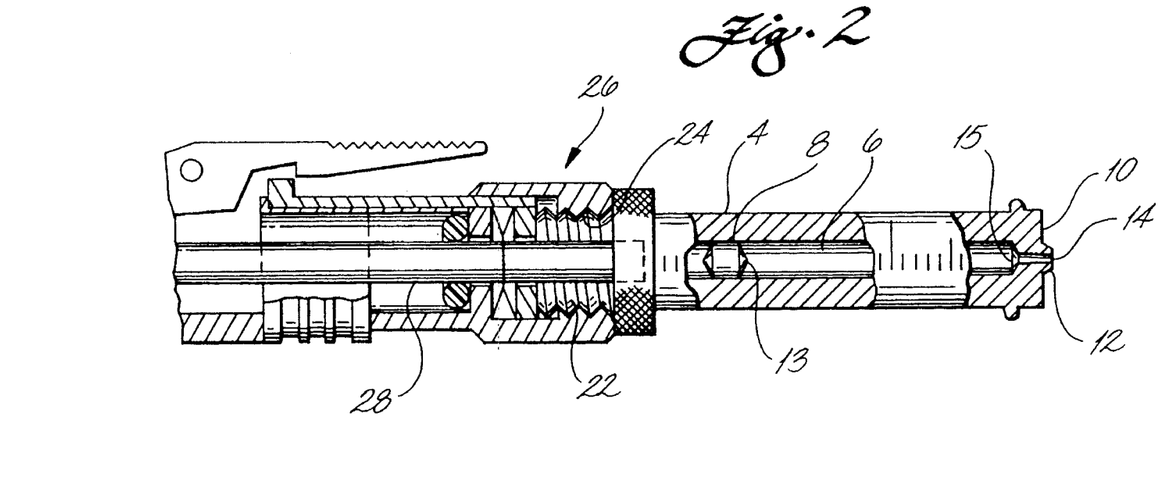
FIG. 2 is a partial cross-sectional side view of a medication ampule coupled to an injection device according to a first embodiment of the invention.

Referring to FIGS. 1 and 2, there is shown in semi-schematic partial cross-section side view, an exemplary embodiment of a medication ampule, and injection device provided in accordance with practice of principles of the invention. The medication ampule generally designated at 2, is illustrated as having an elongated cylindrical shell 4 defining a longitudinal, concentric hollow cylinder 6. Within the hollow cylinder is a plunger 8 which snugly but slidably fits therein forming a high pressure seal around the entire interface of the plunger with the wall of the hollow cylinder. In operation, a "front" end 10 of the ampule comes in contact with skin into which medication is to be injected. (It should be noted that the end 10 of the ampule is arbitrarily designated the "front" end for reference purposes only, and other location terms used herein concerning the ampule, such as "forward", "rear", "rearward" and the like are merely relative to said front end.) Generally the front end 10 is flat except for a centered frusto-conical protrusion 12. This protrusion, when pressed against the skin, tends to form a pocket which is advantageous during the injection process. Centrally defined by the protrusion and the front end is an open tapered orifice 14 which communicates with the hollow cylinder 6 and has a common longitudinal axis therewith, but which is much smaller in diameter. It has been found that an inner diameter of approximately 0.006 inches for the mouth of the orifice is generally suitable for the purposes of this invention. As illustrated the plunger 8 has a slightly tapered front end 13 which generally conforms to a tapered recess 15 defined by the front end wall of the hollow cylinder. The rear end of the plunger has an identical taper for simplicity of installation.

In operation, a liquid (generally medication) is inserted, in proper dosage, into a chamber which is that portion of the hollow cylinder between the ampule front end and the plunger, and the front end of the ampule is pressed against an injection site. The plunger is then driven forward by a linearly applied force and converts this force to pressure on the liquid sufficient to cause the liquid to leave the chamber via the orifice at such a velocity that it can be hypodermically injected at the injection site. The tapered recess 15 preceding the orifice funnels the liquid into the orifice, and the conforming tapered front end 13 of the plunger ensures that all the liquid is ejected.

A preferred method of inserting liquid into the ampule chamber is to mate the front end of the ampule with a device that can communicate liquid under pressure through the front end orifice into the chamber without allowing ambient gas to enter the chamber, the pressure being sufficient to drive the frictionally resisting ampule plunger backward to accommodate (within the capacity of the hollow cylinder with the plunger therein) the amount of liquid being inserted.

Referring again to FIGS. 1 and 2, preferably the ampule shell 14 is transparent to permit viewing of the amount of medication therein, and further has dosage scale graduations 18 along its length with the plunger serving as a marker for setting a proper dose.

Figure 9:
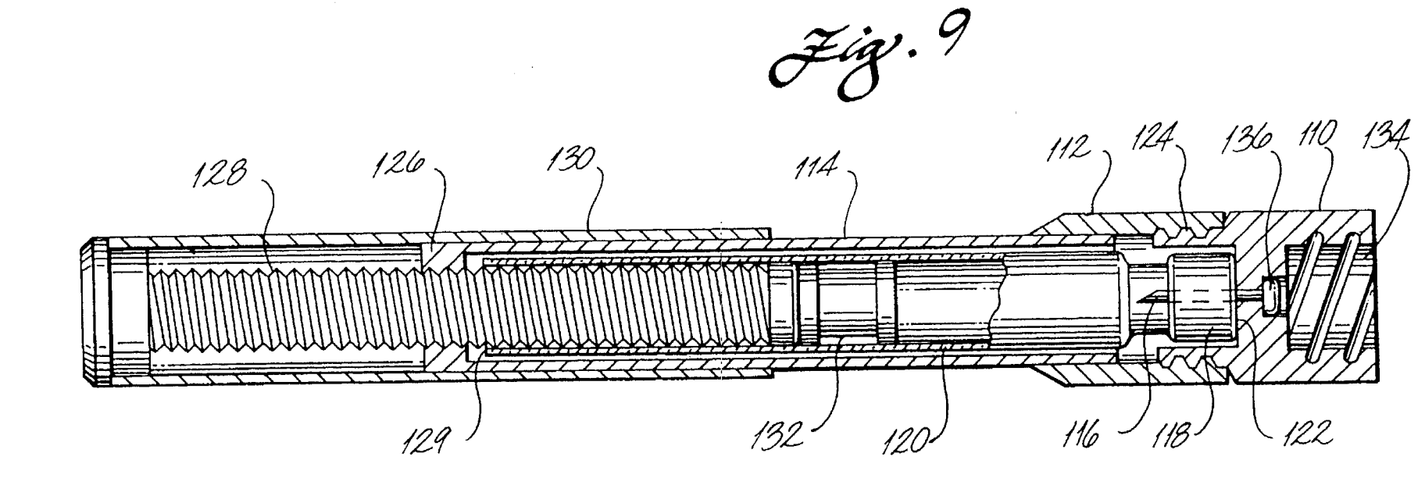
FIG. 9 is a semi-schematic cross-sectional view of a transfer loader and transfer adapter for loading medication into an ampule according to practice of principles of the invention.
Figure 10:
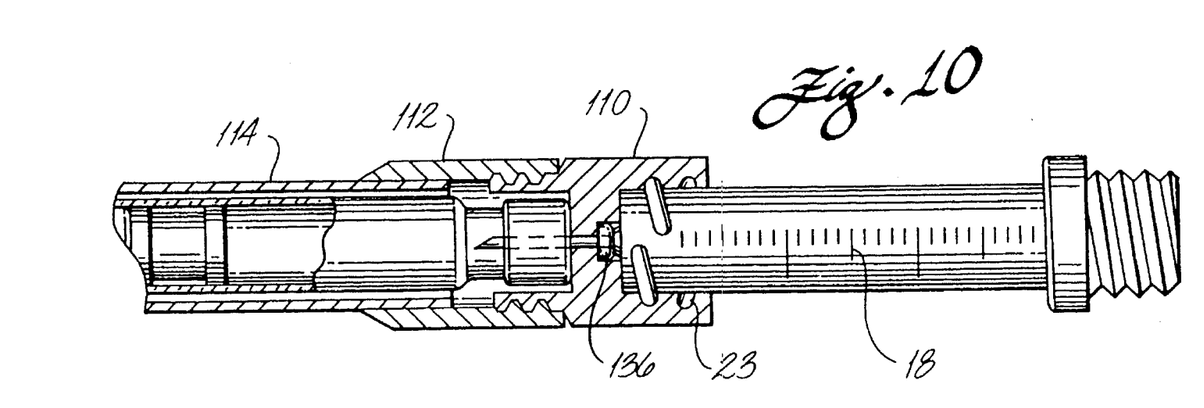
FIG. 10 is a semi-schematic partial cross-sectional view of the transfer adapter of FIG. 9 having a medication ampule coupled thereto.

The hollow cylinder 6 is open at the rear end 20 of the ampule where there are external male threads 22 for engaging a corresponding female threaded opening 24 defined by a head, i.e., a "front" end, of a injector device, generally designated 26. (It should be noted that said end of the injector device is arbitrarily designated the "front" end for reference purposes only, and other location terms used herein concerning the injector device, such as "forward", "rear", "rearward" and the like are merely relative to said front end.) The injector device has therein a thrust rod 28 which in operation is thrust forward from the injector device into the ampule's hollow cylinder 6 to impact the plunger 8 and drive it forward. The thrust rod of the injector device is the means by which force is linearly applied to the plunger to drive it forward to propel the medication out of the ampule's front end orifice 14. The plunger is in effect a movable wall of the chamber which when driven forward forcefully reduces the volume of the chamber. The ampule also has a flat annular ridge 29 projecting therefrom which may be knurled. This ridge provides a finger gripping surface by which a user can screw the ampule into a injector device, via the male threads 22, or for engaging it with a device (such as illustrated in FIGS. 9 and 10) that can communicate liquid under pressure into the ampule through the ampule's front end orifice 14 via front end coupling means 23 which preferably comprises LUER threads common in the art of medicine delivery instruments.

Figure 1A:
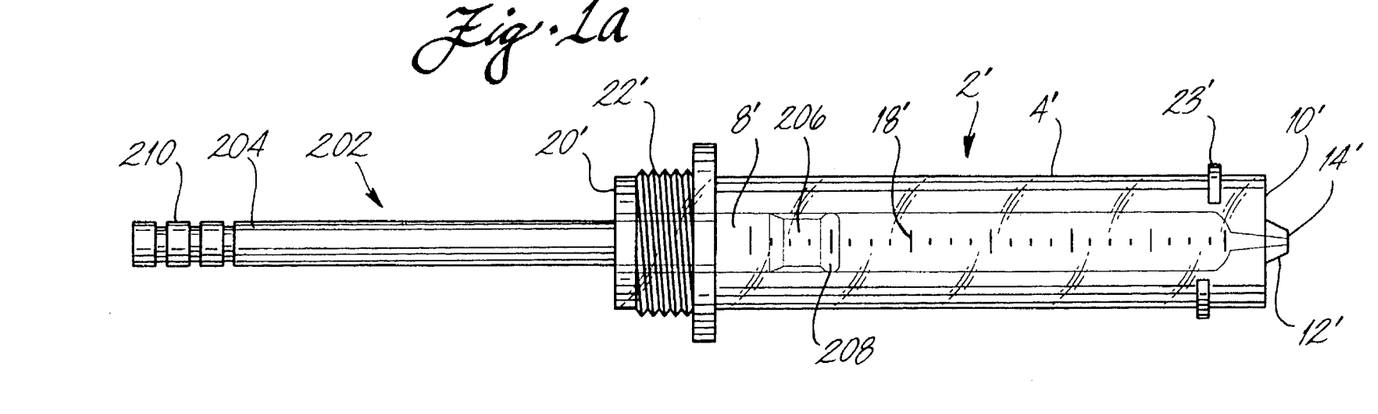
FIG. 1a is a semi-schematic, plan view of a second exemplary embodiment of a medication ampule assembly provided in accordance with practice of principles of the invention.
Figure 2A:
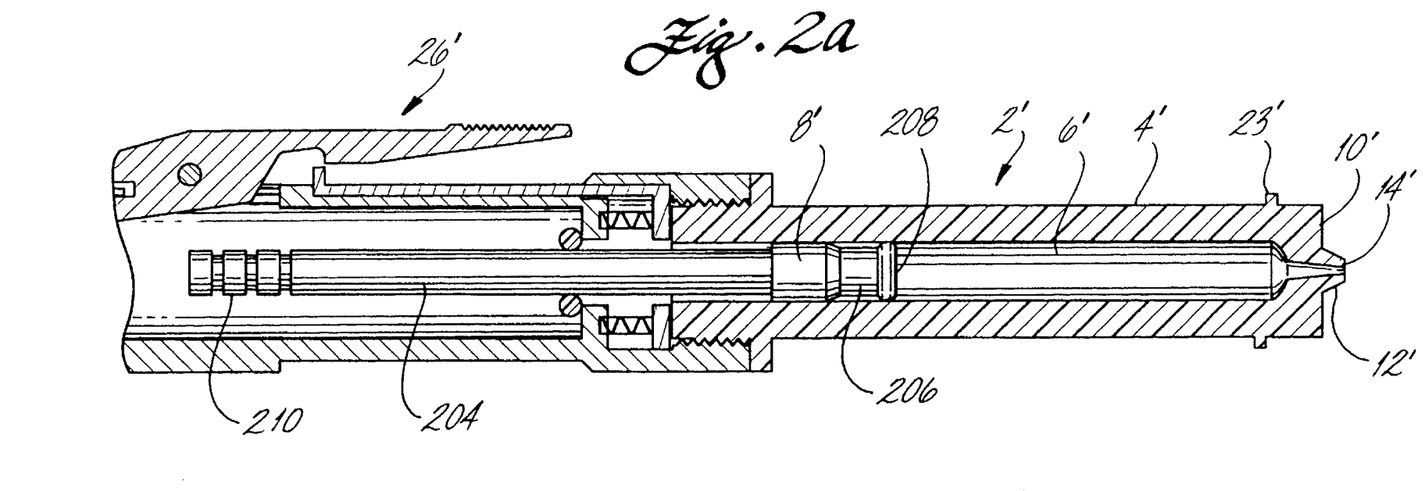
FIG. 2a is a partial cross-sectional side view of a medication ampule assembly coupled to an injection device according to a second embodiment of the invention.

Referring now to FIGS. 1a and 2a, there is shown a semi-schematic partial cross section side view of a second exemplary embodiment of a spring actuated needleless hypodermic injection assembly provided in accordance with practice of principles of the invention, wherein elements similar to those described in connection with the embodiment illustrated in FIGS. 1, 2, 5 and 6 are identified with the same reference numerals, primed.

The injection assembly comprises a hand-held injector device 26', and a refillablep, variable-dose medication ampule assembly 2'. The ampule assembly 2' is configured to be externally mounted on the injector device 26' and operates in conjunction with the injector device to eject liquid medication from the ampule assembly 2' for a needleless hypodermic injection. The ampule assembly is preferably fillable by a user and reusable to a limited extent, i.e., it is used from one to about five times and discarded.

Although the injection assembly can be held in any position, the positions of the components of the assembly relative to one another are described below with the ampule assembly 2' considered to be mounted on the front end of the injector device 26'.

The ampule assembly 2' comprises an elongated tubular body portion 4' (a shell) having an elongated, hollow, cylindrical chamber 6' centrally disposed along the length of the body portion 4' for holding liquid medication (not shown). Although the body portion, or shell, 4' can be fabricated of any suitable material, an inert, injection molded, clear plastic is preferred. The front end 10' of the body portion, or shell, 4' is generally flat except for a centered frusto-conical protrusion 12'. This protrusion 12', when pressed against the skin tends to form a pocket which is advantageous during the injection process. An open tapered orifice 14' is centrally defined by the protrusion 12' and is in communication with the tubular chamber 6' so that liquid medication can be introduced and ejected into and out of the chamber through the orifice.

In the exemplary embodiment of FIGS. 1a and 2a, the back end 20' of the ampule shell 4' is provided with external male threads 22' which, as described below in detail, are used for engaging a corresponding female threaded opening, and thus mounting the ampule assembly on to the injector device 26'. The front end 10' of the ampule shell 4' is provided with coupling means 23' for engaging the ampule assembly 2' with an external device through which liquid medication can be introduced into the tubular chamber 6' through the orifice 14'. The coupling means 23' may be a bayonet-type connection for engagement with an appropriately designed bayonet receptacle, but preferably comprises male LUER-type threads common in the art of medication delivery systems.

A plunger assembly, indicated generally at 202, suitably comprises a plunger handle 204 and a plunger piston 8', mounted on the forward end of the plunger handle, and which is snugly but slidably disposed within the cylindrical chamber 6', therein forming a seal around the interface between the plunger piston 8' and the interior wall of the cylindrical chamber 6'. The plunger piston is preferably constructed of an inert, flexible material such as rubber or plastic, or the like.

In the exemplary embodiment, the plunger piston 8' has a recessed groove 206 circumferentially provided around its front end in order to define a flange 208 on its front end. The plunger piston 8' and, particularly, the flange 208 preferably have outside diameters slightly larger than the inside diameter of the cylindrical chamber 6'. When the plunger assembly is inserted into the cylindrical chamber 6', the plunger piston 8', and particularly the flange 208, is compressed and thereby forms an air-tight and liquid-tight seal between the plunger piston and the interior walls of the cylindrical chamber.

The plunger handle 204 extends out of the cylindrical cavity 6' from the back end 20' of the ampule shell 4', and is preferably of a length such that when the plunger assembly is fully inserted into the cylindrical chamber 6' a portion of the plunger handle 204 remains extended out from the back end 20' of the ampule assembly. The plunger handle 204 includes a ribbed feature comprising annular indentations 210, provided so that the plunger handle may be securely gripped by a person using the ampule assembly to thereby move the piston 8' back and forth within the cylindrical chamber 6' in order to fill the chamber with the medication or eject medication from the chamber through the orifice 14'.

In operation, liquid medication is introduced, in proper dosage, into the cylindrical chamber between the front end 10' of the body portion and the plunger piston 8'. The front end of the ampule assembly is pressed against an injection site and the plunger assembly is driven forward by a linearly applied force. The plunger assembly converts this force to a corresponding pressure on the liquid medication sufficient to cause the liquid to be ejected from the chamber via the orifice at such a velocity that it can be hypodermically injected at the injection site.

As in the embodiment described in connection with FIGS. 1 and 2, the ampule assembly shell 8' is transparent to permit viewing of the amount of medication therein, and further includes dosage scale graduations 18' along its length against which the plunger acts as a marker to determine a proper medication dose.

Figure 5:
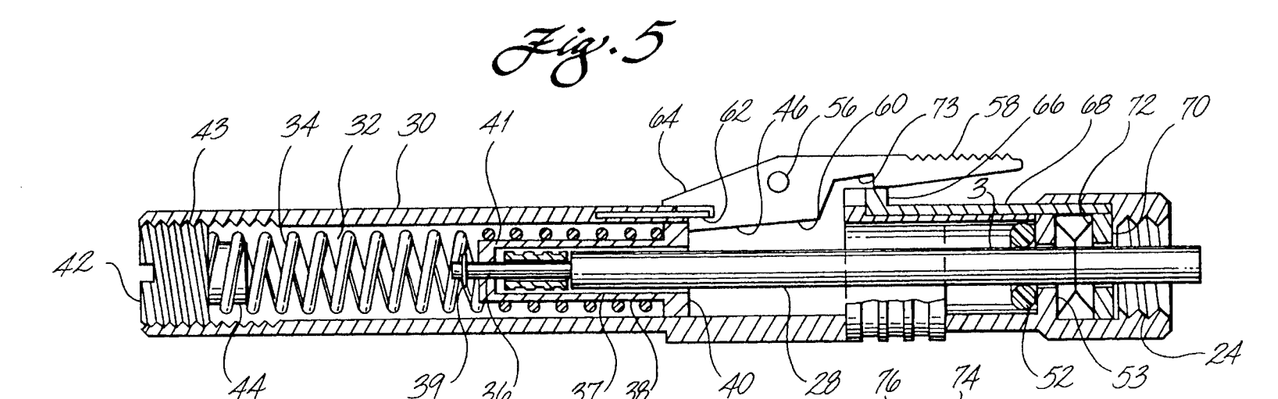
FIG. 5 is a semi-schematic cross-sectional side view of a first embodiment of an injector device in the cocked position provided in accordance with the present invention.
Figure 6:
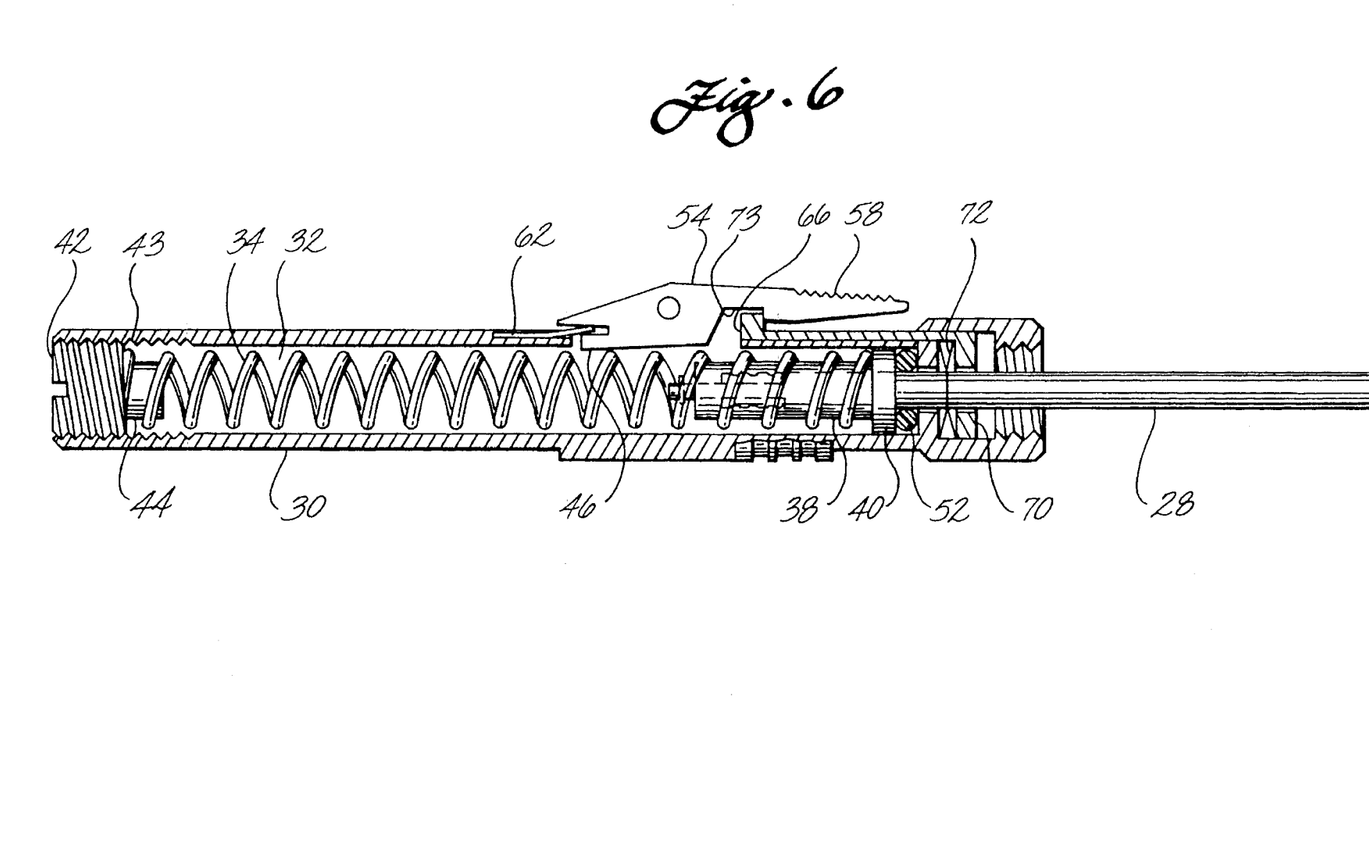
FIG. 6 is a semi-schematic cross-sectional side view of the injector device of FIG. 5 in the fired position.

Referring now to FIGS. 5 and 6, there is shown in semi-schematic, cross section side view, a first exemplary embodiment of a spring-actuated needleless hypodermic injector device 26 provided in accordance with practice of principles of the invention. The injector device 26 is illustrated as having an elongated cylindrical housing 30 defining a longitudinal channel 32 in which is disposed a coiled spring 34, a thrust rod 28, and means for transferring linear force exerted by the spring, when expanding axially to the thrust rod. Preferably the longitudinal axis of the spring and the thrust rod are collinear. A rear length 36 of the rod has a diameter smaller than the remaining, forward length 37 of the rod, and annular to most of this rear length and part of the forward length is a sleeve 38 having an inner diameter slightly larger than the forward length of the rod and an outer diameter slightly smaller than the inner diameter of the coiled spring 34. The sleeve occupies an annular space between the forward length of the thrust rod and the coiled spring, keeping the rod and spring aligned. At the front end of the sleeve is an outwardly projecting, annular flange 40 which presents a shoulder against which a forward end of the spring abuts. At the rear end of the sleeve is an inwardly projecting, annular flange 41 which essentially closes the sleeve except for an opening through which the rear length 36 of the thrust rod extends. In the annular space between the sleeve 38 and the rear length 36 of the rod is an elongated annular shock absorber 48. The rear end of the coiled spring abuts a means for adjusting the compression force of the spring. Preferably this adjustment means is a screw 42 which engages female threads 43 at the rear end of the channel 32. The screw closes the rear end of the channel and is used to selectively shorten or lengthen the channel. The rear end of the spring abuts the foot of the screw and the front end of the spring abuts the annular flange 40. A stud 44 projecting from the foot of the screw keeps the abutting end of the spring centered. The sleeve is kept in relation to the rod by a retaining ring 39 secured at the end of the rear length 36.

In the exemplary embodiment illustrated in FIGS. 5 and 6, the adjustment means suitably comprises a set screw, but any means which can selectively shorten or lengthen the channel in which the compression spring is confined can be used. For example, a finger turnable screw, i.e., a screw having a knurled knob or flange around its head, can be used in place of the set screw without departing from the scope of this invention.

As depicted in FIG. 5, the coiled spring 34 is illustrated in a compressed state. It is held in this compressed state by a latch 46 which protrudes into the channel 32 and catches the sleeve's front flange 40. When the latch is removed from obstructing movement of the sleeve the coil acting against the sleeve will cause it to move forward. The sleeve's rear flange 41 will impact and act against the shock absorber 48 which in turn will act against a shoulder created by the difference in diameters between the rear and forward lengths of the rod 28. In this way, the force of the expanding spring is linearly exerted against the thrust rod. Preferably the shock absorber is made from resilient material such as rubber or rubber-like material. The expanding spring will drive the rod forward until the forward face of the sleeve 38 encounters a cushion 52 affixed to a wall 53 at the front extremity of the channel 32. As illustrated, this cushion is in the form of an "O" ring having a hollow center to allow passage of the rod therethrough. The front wall 53 of the channel defines a passageway through which the rod can likewise extend. Thus when the ampule is engaged with the injector device, there is a continuous passageway through the cushion 52, through the front wall of the channel 32, and into the ampule so that the rod can drive the ampute plunger 8.

The cushion 52 at the front wall 53 of the channel cushions the impact of the sleeve 38 against the wall. It suppresses the noise of the collision and prevents thumping. It also reduces wear on the instrument. The cushion can be made from rubber or any other suitable resilient, energy-absorbent material.

The shock absorber 48 softens the impact of the rod against the ampule plunger. This is especially useful for ampules containing small doses of medicine. In such cases the plunger is further forward in the ampule and therefore the stroke of the rod (the distance the rod travels before encountering the plunger) is greater. With a greater stroke the rod develops a greater velocity and hits the plunger harder. The shock absorber momentarily absorbs some of the energy being delivered by the rod sleeve 38 when the rod first hits the plunger and thus it softens the impact on the plunger. This keeps the initial instantaneous pressure applied to the medicine at a level safely within ampule structural limits.

Referring again to FIGS. 5 and 6, after the injector device has been fired, the device is in an un-cocked condition (FIG. 6). The sleeve's front flange 40 is forward of the latch 46. In order to cock the injector device, the thrust rod is pushed backward, by any suitable means (such as by the device illustrated in FIGS. 7 and 8), until the sleeve's front flange is caught by the latch (as is seen in FIG. 5). Preferably the latch is disposed at the end of a lever 54 which pivots about a pin 56 journaled in a clevis 57 (shown in FIGS. 3 and 4) affixed to the housing 30, the opposite end of the lever being a trigger 58 having a flat knurled surface and disposed to be finger actuated. As the rod is being pushed backward during a cocking operation, the front flange 40 encounters a beveled surface 60 on the underside of the lever, the underside of the latch being part of the beveled surface. As the rod is pushed further rearwardly, the sleeve flange 40 rides against the beveled surface and causes the latch to pivot out from the channel 32 to at least an extent necessary to permit passage of the sleeve flange 40. As the latch pivots out of the channel it bends a normally flat leaf spring 62 which projects over a top side of the latch. Once the sleeve's front flange is pushed back beyond the beveled surface, the resilience of the leaf spring causes the latch to re-enter the channel and present an obstruction to forward movement of the sleeve. A stop 64 prevents the latch end of the lever from pivoting too far into the channel. Forcing the rod backward causes the coiled spring to accumulate energy which is stored in the spring until it is released.

Figure 5A:
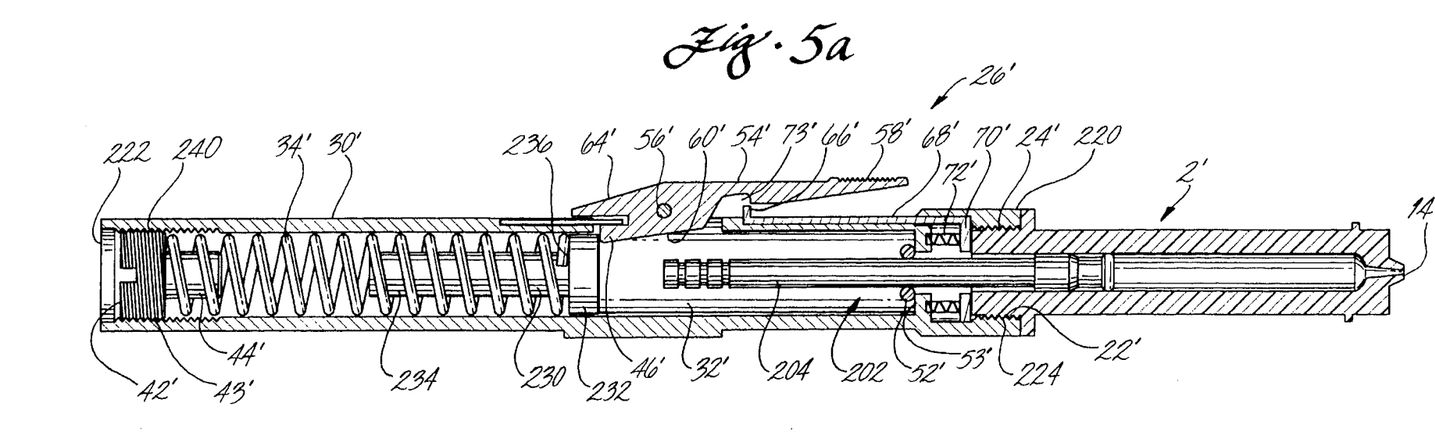
FIG. 5a is a semi-schematic cross-sectional side view of a second embodiment an injector device in the cocked position provided in accordance with the present invention.
Figure 6A:
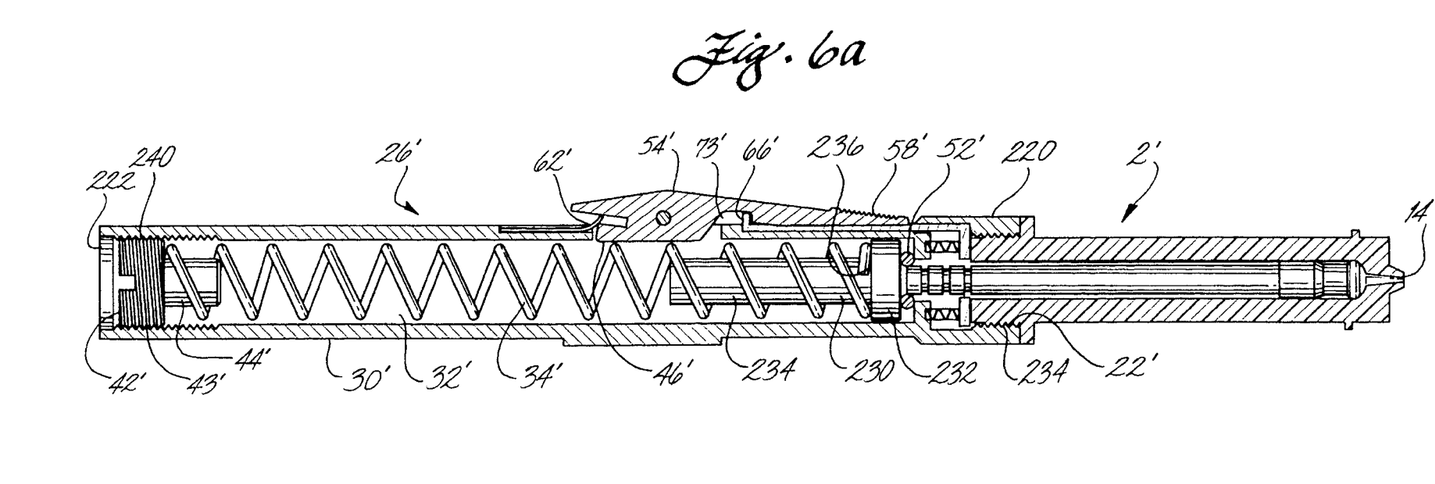
FIG. 6a is a semi-schematic cross-sectional side view of the injector device of FIG. 5a in the fired position.

Referring now to FIGS. 5a and 6a, there is shown in semi-schematic, cross section side view, a second exemplary embodiment of a spring actuated needleless hypodermic injector device 26' provided in accordance with practice of principles of the invention, wherein elements similar to those described in connection with the embodiment illustrated in FIGS. 5 and 6 are identified with the same reference numerals, primed. The injector device 26' is configured to receive the ampule assembly 2' when the ampule assembly is filled with liquid medication, and to provide the force which drives the plunger assembly 202 forward toward the orifice 14'.

The injector device 26' suitably comprises an elongated cylindrical housing 30', open at its forward or front end 220 and closed at its back end 222 and defining a cylindrical longitudinal channel 32'. The injector device housing 30' can be formed of metal or a suitable plastic material, as desired. The housing front end 220 is configured to receive and mount the ampule assembly 2'. In the exemplary embodiment, threads 224 are provided in the front end 220 of the housing 30' which mate with the threads 22' on the ampule shell to provide a mounting for the ampule in the injector device 26'.

A piston 230 is mounted in the housing 30' for slidably moving along its length and is biased toward the front end 220 of the housing 30' by a coiled spring 34'. The piston 230 has a front bearing flange 232 which has an outer diameter slightly smaller than the inner diameter of the housing 30', and a back portion 234 extending coaxially rearward from the bearing flange 232 and which has an outer diameter slightly smaller than the inner diameter of the coiled spring 34'. The junction between the piston bearing flange 232 and back portion 234, thus, defines an annular surface 236 which presents a shoulder against which a forward end of the coiled spring abuts.

The back end of coiled spring 34' abuts a removable plug 42' which includes threads 240 which engage threads 43' provided on the inside wall of the back end of the housing 30'. The removable plug 42' thus closes the rear end of the channel 32' and is threadably used to selectively lengthen or shorten the channel. The back end of the coiled spring 34' abuts the plug base and fits, in an annular fashion, over a cylindrical extension, or stud, 44' provided at the center of the plug base.

Thus, in the illustrated embodiment, the removable plug 42' is depicted as a set screw which suitably comprises adjustment means for selectively lengthening or shortening the longitudinal channel in which the coiled spring 34' is confined and, thus, selectively adjusting the tension on coiled spring 34'. Although preferably a set screw, a finger turnable screw, e.g., a screw having a knurled knob or flange at its back end may be used without departing from the scope of the invention.

In the illustrated embodiment of FIGS. 5a and 6a, the coiled spring 34' is held in a compressed state by a latch 46' which protrudes into the longitudinal channel 32' and is disposed against the bearing flange 232 of the piston 230. When the latch 46' is released, the coiled spring acting against the piston 230 forces the piston towards the front end 220 of the channel 3240 . The piston's bearing flange 232 will impact the plunger handle 204 of the ampule assembly, drive it forward and thus eject liquid medication from the ampule assembly 2' through orifice 14'.

The expanding spring will drive the piston 230 forward until the bearing flange 232 of the piston encounters a resilient cushion 52' affixed to a wall portion 53' at the forward extremity of the longitudinal channel 32'. In the illustrated embodiment, the resilient cushion 52' is preferably an "O" ring having a hollow center to allow passage of the plunger handle 204 therethrough. The wall portion 53' of the longitudinal channel 32' likewise defines an opening through which the plunger handle 204 may extend into the longitudinal channel 32'. Thus, when the ampule assembly 2' is engaged with the injector device 26' there is a continuous passage way through the wall portion 53' and the resilient cushion 52' and into the longitudinal channel 32' so that the plunger handle may be presented to the piston 230 and may be driven by the piston so as to inject medication.

In a preferred embodiment of the injection device 26' provided in accordance with practice of principles of the invention, the latch 46' is disengaged from the bearing flange 232 of the piston 230 by depressing a trigger lever 54' which pivots about a pin 56' journaled in a clevis (not shown) affixed to the housing 30'. The coiled spring is released by pressing down on the trigger lever 54' at a trigger 58', located at a forward end of the lever 54' opposite the latch 46' which causes the lever to rotate about pin 56' and move the latch 46' out of the channel 32', thus disengaging the latch from the bearing flange 232 of the piston 230. The trigger lever is biased to its unactuated, or cocked, position by means of a leaf spring 62' mounted on the housing 30'. The spring 62' extends upwardly from the housing so that its curved upper end projects over and contacts a top surface of the latch 46'. When the injector device is reset by a suitable cocking operation, as described in more detail below, the piston 230 is forced towards the back end 222 of the channel 32' until its bearing flange 232 is forced beyond the position of latch 46'. The resilience of the leaf spring 62' causes the latch 46' to reenter the channel and present an obstruction to forward movement of the piston 230. Forcing the piston backward causes the coiled spring 34' to accumulate energy which is stored in the spring until it is again released by depressing the forward end 58' of the trigger lever 54'.

Referring now to the embodiments depicted in FIGS. 5, 5a, 6 and 6a, an automatic interlock safety is provided which is the same for both embodiments and is described in connection with both embodiments. Unprimed reference numerals refer to the first embodiment of FIGS. 5 and 6, and primed reference numerals refer to the second embodiment of FIGS. 5a and 6a.

The coiled spring 34, 34' can be released by pressing down on the trigger 58, 58' which causes the lever 54, 54' to rotate about pivot pin 56, 56' and move the latch 46, 46' out of the channel 32, 32' and out of the way of the sleeve 38, or piston bearing flange 232. To prevent inadvertent triggering of the injector device, there are two safety mechanisms. As illustrated, one safety mechanism is automatically in place whenever the injector device does not have an ampule engaged thereto. This safety will not allow the injector device to be triggered until an ampule is fully screwed into the head of the unit. This safety has a blocking means which jams the trigger to prevent downward rotation thereof. This blocking means is a protrusion 66, 66' which is normally lodged between the trigger and the housing 30, 30'. The protrusion is connected to one end of a movable arm 68, 68', the other end of which is connected to one end of a movable ring wall 70, 70' which defines a central opening through which the rod extends. This ring wall is spaced from and disposed forward of the relatively immovable wall 53, 53' at the front extremity of the channel 32, 32'. Between the relatively immovable wall 53, 53' and the movable wall 70, 70' is a compressible spring means 72, 72', such as small coiled springs, leaf springs, a star washer, or the like. Normally the compressible spring biases the ring wall forward enough for the protrusion 66, 66' to jam the trigger thereby preventing actuation thereof. However whenever an ampule is fully screwed into the threads 24, 24' of the injector device, the rear end of the ampule pushes the ring wall back far enough to remove the protrusion as an obstruction to movement of the trigger, thereby releasing this first safety. As illustrated, the ampule pushes the protrusion 66, 66' back until it aligns with a recess 73, 73' under the trigger, which alignment allows the trigger to be sufficiently actuated to release the thrust rod, and fire the injector device. Thus by this first safety, a user cannot release the thrust rod, and cause possible injury to self or others, without having an ampule fully engaged with the injector device.

Figures 3, 4:
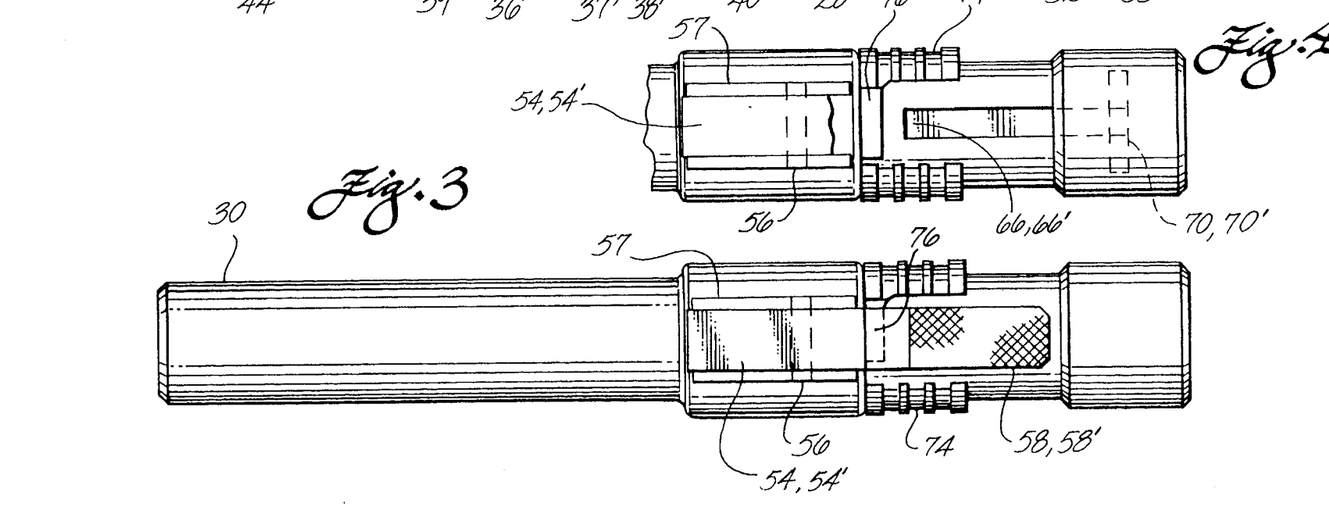
FIG. 3 is a top plan view of first and second embodiments of an injector device according to practice of principles of the invention.
FIG. 4 is a partial top plan view of the injector device depicted in FIG. 3.

Referring now to FIGS. 3 and 4, a manual safety ring 74 is shown which prohibits movement of the actuating lever from its unactuated to its actuated position when the safety is in the "locked" position. In the preferred embodiment shown in FIGS. 3 and 4, the manual safety is the same for both embodiments of the injection device, described above, and is described in connection with both embodiments. The manual safety ring 74 is mounted annular to the housing 30, 30' beneath the trigger portion 58, 58', of the trigger lever 54, 54' and can be rotated about an axis collinear with the long axis of the housing 30, 30'. When the manual safety ring 74 is rotated about its axis, a tongue 76 is rotated into a position beneath the trigger 58, 58' so as to interpose the tongue 76 between the trigger and the housing 30, 30'. The trigger 58, 58' is thereby prevented from being depressed to its actuated position.

When the manual safety ring 74 is rotated in the other direction, tongue 76 is removed as an obstruction between the trigger 58, 58' and the housing 30, 30'. The trigger 58, 58' is free to be depressed, thus actuating the injector device, assuming, of course, that an ampule assembly is in place and the automatic safety has been disengaged.

An additional feature of the manual safety ring 74 depicted in FIGS. 3 and 4, is that annotations may be provided in the housing 30, 30' which are masked, and unmasked, by rotation of the manual safety ring 74. Such annotations may include text which indicates that the injector device is "safe" when the safety ring 74 has been rotated in a manner to place the tongue 76 beneath the trigger 58, 58', or "un-safe", when the safety ring 74 has been rotated to remove the tongue 76 as an obstruction from beneath the trigger 58, 58'. Thus, the manual safety ring 74 in combination with such text, provides an indication of the safety status of the injector device.

In accordance with practice of the principles of the invention, the trigger is disposed on the side of, and aligned generally parallel with the long axis of the injector device, and this has distinct advantages over other locations for the trigger. With this invention, a user can apply pressure to an injection site by, for example an index finger, and independently adjust pressure on the skin without inadvertently triggering the unit. Moreover, a person administering an injection to another person can more conveniently hold and trigger the unit.

Referring now to the embodiments illustrated in FIGS. 6 and 6a, the trigger 58, 58', of an un-cocked or fired injector device, is in a generally depressed state with the first safety's protrusion 66, 66' captured in the trigger's recess 73, 73'. It is held that way because the coiled spring 34, 34' biases the latch 46, 46' from fully re-entering the channel 32, 32', and so the lever 54, 54' is blocked from rotating (counterclockwise per the illustration) sufficiently for the trigger to return to its firing position (as illustrated in FIG. 5) and for the first safety's protrusion to be released. When the injector device is being cocked, the latch 46, 46' is free to fully re-enter the channel under the influence of the leaf spring 62, 62'. This re-entry causes the trigger to rise and release the first safety's protrusion 66, 66'. Thus at essentially the same moment the injector device is cocked, the first safety engages.

As an additional advantage of the illustrated embodiment of the invention, the injector device and ampule combination can be designed to administer very small doses of medication by simply providing ampules with a smaller internal diameter and a injector device having a correspondingly smaller diameter thrust rod, while keeping all outer dimensions constant. The smaller ampule internal diameter results in an extended dosage scale providing greater accuracy in setting the dosage. This is a highly desirable feature in such applications as delivering small doses of medication to children.

Figure 7:
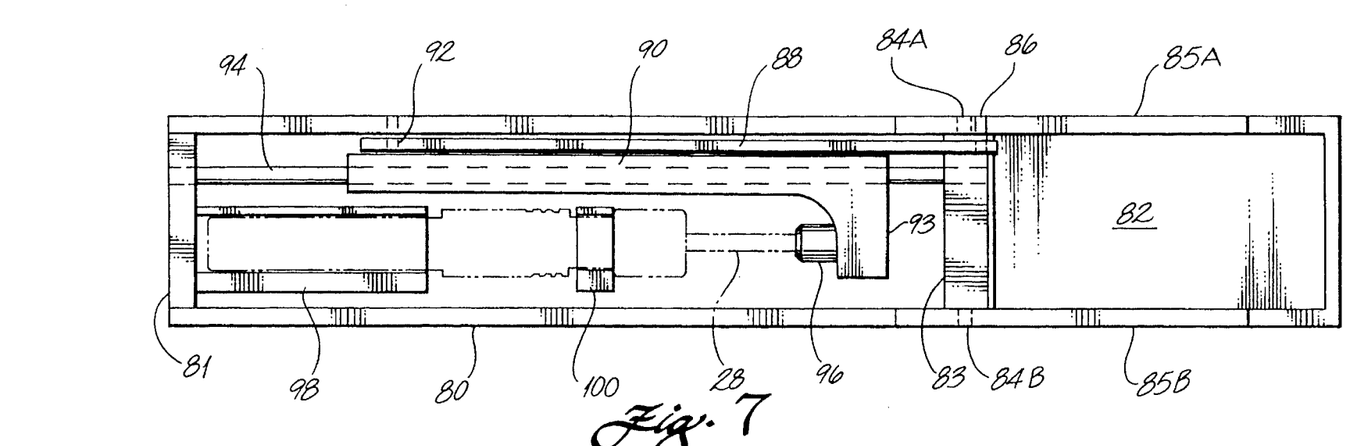
FIG. 7 is a semi-schematic top plan view of a first embodiment of a cocking/carrying case provided in accordance with the present invention.
Figure 8:
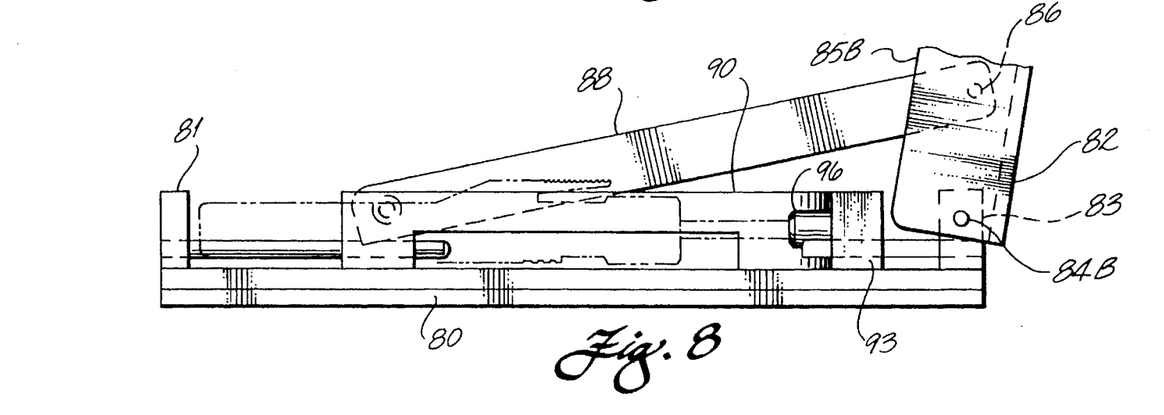
FIG. 8 is a semi-schematic cross-sectional side view of the cocking/carrying case of FIG. 7.

Referring to FIGS. 7 and 8, there is shown an injector device cocking/carrying case which automatically cocks the first embodiment of the injector device of FIGS. 5 and 6 while closing the case. The case, which can be also called a "reset box," has an elongated rectangular base 80. At one end of the base is a narrow wall 81 projecting up from the base. A cover 82 is hinged to an opposite narrow wall 83 also projecting up from the base, the connection is by means of hinge pivots 84A and 84B. The cover has side walls, 85A and 85B, projecting therefrom, and when closed the cover forms the top and the two long sides of the rectangular case with the narrow walls closing the case at its ends. Pivotally connected to a cover side wall 85A by a linkage pivot 86 is one end of a linkage bar 88. The opposite end of the linkage bar is pivotally connected to an elongated shuttle member 90 also by a linkage pivot 92. The shuttle member slides back and forth, driven by the linkage bar, along a slide bar 94 which extends from and between the case's end walls and is parallel to the long axis of the case. Projecting from the shuttle member at an end closest to the cover hinge is a leg 93 and affixed to the leg is a pillow 96. Alongside the shuttle's path and affixed to the base is a cradle 98 adapted to seat a rear portion of the injector device. A neck cradle 100 also affixed to the base is adapted to seat that portion of the injector device immediately behind the unit's head. This neck cradle ensures that the second safety (74 of FIG. 4) is disengaged in order to allow cocking of the unit. Lying in the cradles, an injector device is longitudinally parallel to the path of the shuttle member and the pillow 96 of the shuttle aligns with the injector device's thrust rod 28. When the cover is fully opened the leg of the shuttle is pulled to an end of the case to allow room for inserting an uncocked injector device into its cradles. During the course of closing the cover, the leg traverses toward the injector device's extended thrust rod until it contacts it. As the cover is further closed, the shuttle leg pushes the thrust rod back into the injector device. This continues until the injector device is cocked and the cover is closed. The cover and the linkage bar can thus be seen to provide sufficient mechanical advantage to make cocking a injector device an easy operation.

Figure 7A:
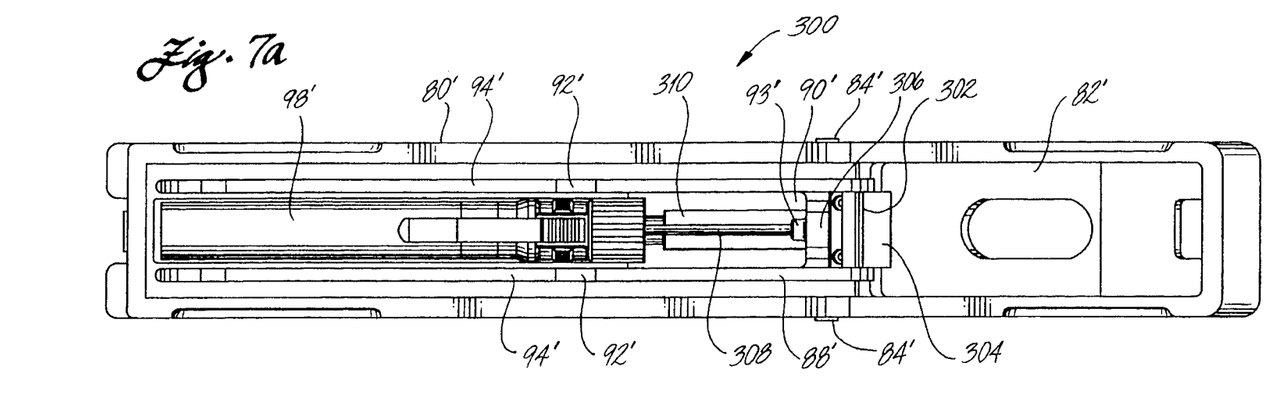
FIG. 7a is a semi-schematic top plan view of a second embodiment of a cocking/carrying case provided in accordance with the present invention.
Figure 8A:
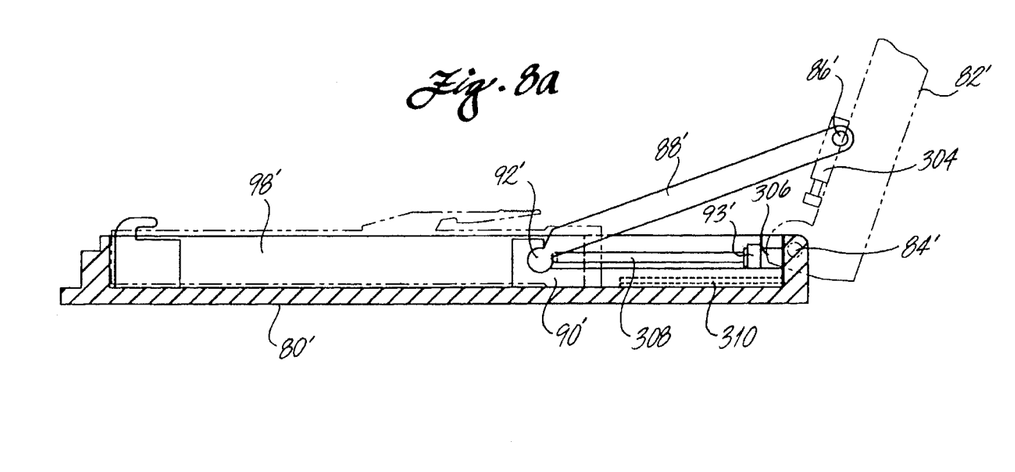

A second embodiment of a cocking/carrying case, used to cock the injector device of FIGS. 5a and 6a, is provided in accordance with practice of principles of the invention and is described in connection with FIGS. 7a and 8a. The cocking/carrying case indicated generally at 300, includes two linkage bars 88' connected together at a top end by a hinge pin 86' which is, in turn, held in an elongated slot 302 provided in a pivot block 304 which is affixed to the underside of an elongated, rectangular cover 82'. The opposite end of each linkage bar 88' is connected to an elongated shuttle member 90' by a linkage pivot 92'. The shuttle 90' slides back and forth, driven by the linkage bars, along slide tracks 94' which extend adjacent to the outside edges of an elongated, rectangular base 80' and are disposed parallel to the long axis of the rectangular case 300. The shuttle member includes a saddle 306 disposed at an end closest to the cover. Projecting from the saddle 306 is an extension 93' to which a ramrod 308 is attached. A bearing surface 310 is provided on the base 80' at the end of the base adjacent the cover. The bearing surface 310 supports the shuttle saddle as the shuttle is slid back and forth within the case 300, in a manner which supports the saddle 306 and attached ramrod 308.

An injection device, such as the device of FIGS. 5a and 6a, is placed in an elongated cradle 98' defined by the exterior walls of the base 80', and is positioned longitudinally, to be along the path of the shuttle 90'. The saddle 306 and attached ramrod 308 are positioned by bearing surface 310 such that the ramrod 308 is aligned with the openings provided in the front part of the injection device.

When the cover is fully opened the linkage bars pull the shuttle to the back end of the case to allow room for inserting an uncocked injector device 26' into the cradle. As the cover is closed, the linkage bars engage the shuttle pushing the shuttle in the direction of the closing cover until the ramrod 308 contacts the bearing flange 232 of the piston 230 inside the injection device's housing 30'. As the cover is further closed, the shuttle 90', pushed by the linkage bars 88', forces the ramrod 308 into the longitudinal channel 32' of the injection device, thus forcing the piston 230 towards the back end of the channel until the piston's bearing flange 232 clears the end of the trigger latch 46', thus causing the leaf spring 62' to bias the trigger latch 46' into the latched position and retain the piston 230 against forward motion. The injector device is now cocked and the cover 82' to the carrying case 300 may now be fully closed and secured.

The cover 82' and linkage bars 88', thus, combine to provide a mechanical advantage to provide sufficient force to enable the ramrod 308 to force the injection device's piston 230 back against the pressure of the release coiled spring 34'. The mechanical advantage is provided by the cover acting as a lever arm which forces the linkage bars forward during a first portion of its arcuate closure travel. As the injection device's coiled spring is progressively compressed, the force required for additional compression is naturally greater. Accordingly, near the end of the shuttle's travel, where the force to compress the spring is greatest, the mechanical advantage provided by the cover lever arm is also greatest. Thus, the cover and linkage bars combine to provide sufficient mechanical advantage to make cocking an injector device an easy operation. This is an especially important feature for persons with limited physical ability such as the elderly and the very young.

The cocking/carrying case is an important element of the system presented herein. It has been found that the coiled spring needs to develop approximately 30 pounds or greater of force in order for the system to sufficiently work on people with a wide range of skin thickness. Therefore a cocking device with mechanical advantage is for all practical purposes necessary.

Referring to FIGS. 9 and 10, a means for injecting medication, i.e., loading an ampule is illustrated. Medication, e.g. therapeutic insulin is available for home health care in generally two types of containers: a standard vial, usually containing 10 ml of the drug, and syringe cartridges containing 1.5 ml or 3 ml fluid. The ampule loader according to this invention is designed to transfer medication from the conventional syringe cartridges to an ampule. As illustrated it is a pen-size permanent instrument having a small disposable adapter 110 which screws onto the head 112 of the tubular body 114. A canula 116 in the adapter pierces the conventional rubber stopper 118 of a conventional syringe cartridge 120 which is inserted into a recess 122 defined by the adapter. Adapter and cartridge are then inserted into the tubular loader body 114 and secured in place by screw engagement 124. A base 126 of the loader body defines a threaded opening which engages a jack screw 128. The diameter of the jack screw allows it to extend into the conventionally open base 129 of the syringe cartridge. A shroud 130 affixed to a remote end of the jack screw encloses the jack screw and partially sleeves the rear end of the tubular body. The jack screw is turned by grasping and axially rotating the shroud. The length of the jack screw is sufficient to force syringe cartridge's rubber stopper 132 forward enough to eject substantially all the cartridge's liquid contents through the canula. At an end of the adapter opposite the syringe cartridge recess 122 is a recess 134 having LUER type threads for mating with the LUER threads 23 on the front end of the ampules. At the base of this recess 134 is a seat 136 defining a centered perforation (not shown) communicating with the canula. When an ampule is engaged with the adapter, as illustrated in FIG. 10, the frusto-conical protrusion 12 (FIG. 2) of the ampule aligns with and presses against the seat which seals a liquid communication path between the canula and the ampule.

Referring again to FIGS. 9 and 10, to use the ampule loader, an ampule is attached to the adapter by means of the LUER type threads. Then by rotating the jack screw shroud, the syringe cartridge's stopper is forced forward and liquid is forced through the canula and into the ampule, causing the ampule's plunger (13 of FIG. 2) to move back along the scale 18 to a desired dose setting. When the contents of the syringe cartridge are expended (usually about 10 injections) the cartridge and adapter are discarded and a new combination of cartridge and adapter is installed into the loader body. The loader is designed such that the cartridge and the adapter attached to the cartridge stays in the loader body until the medication in the cartridge is used up.

Figure 11:
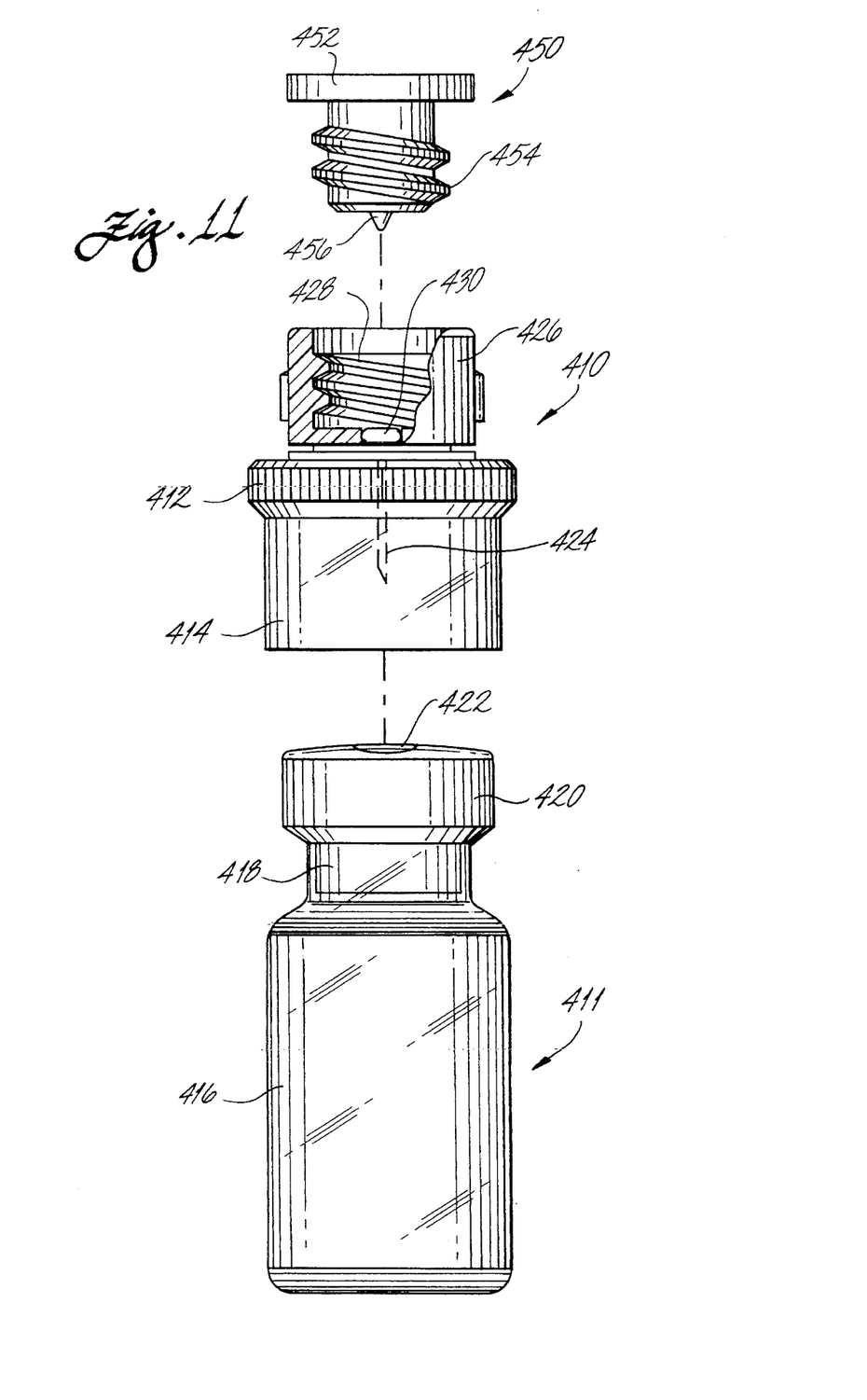
FIG. 11 is a semi-schematic exploded perspective view of a medication vial and vial coupler for coupling the medication vial to an ampule assembly according to practice of principles of the invention.

Referring to FIG. 11, a vial coupler 410, provided to couple the ampule assembly 406 to a conventional medication vial 411 is illustrated in semi-schematic, exploded side view. Vial coupler 410 is provided so that a user does not have to manipulate a needle through a self sealing lid of the medication vial each time it is desired to withdraw a quantity of medication from the vial 411.

The vial coupler 410 includes a generally cylindrical body portion 412 extending into a cylindrical hollow cavity, or shroud 414, which is dimensioned to fit over a standard medication vial 411. In this regard, the vial 411 has an enlarged lower portion 416 which contains medication, a narrower neck portion 418 and a lid portion 420 that is slightly enlarged in relation to the neck portion 418. The lid portion 420 is covered with a self-sealing membrane 422 which is self-sealing in the conventional sense, in that it can be pierced by a canula such as a hypodermic needle, and when the canula is removed the resulting hole in the membrane 422 closes by itself.

The vial 411 may be a conventional ten milliliter medication bottle containing, for example, insulin. The bottle may be about five centimeters high, with the lower portion 416 about two and one-half centimeters in diameter, the neck portion 418 about one centimeter in diameter, and the lid portion 420 about one and one-half centimeters in diameter. These dimensions are commonly used by vial manufacturers, and are, of course, approximate. They are provided only to the extent that the shroud cavity 414 of the vial coupler 410 must be dimensioned accordingly.

The shroud cavity 414 is dimensioned and arranged to receive the lid portion 420 of the vial 411 when the shroud is placed over the lid portion of the vial. As this is done, a cannula 424 pierces the self-sealing membrane 422, to provide a passage through which to convey medication. The cannula 424 extends through the body portion 412 and is positioned in the shroud cavity with its point extending a sufficient distance into the shroud cavity to pierce the membrane 422 when the coupler 410 is on the vial 411.

A locking collar 426 extends from the body portion 412 of the vial coupler in a direction opposite the shroud cavity 414. An interior thread 428 is provided on locking collar 426 for use in coupling the vial coupler 410 to, for example, the front end of an ampule assembly such as ampule assembly 2' of FIG. 1A. For this purpose, threads 428 are preferably LUER-type threads for mating with the LUER threads of the coupling means (23' of FIG. 1A) on the front end of ampule assembly 2'.

A gasketed seal 430 is provided at the base of the locking collar 426 where the cannula 424 extends through the vial coupler body portion 412. When an ampule assembly is engaged with the vial coupler, the frusto-conical protrusion (12' of FIG. 2a) of the ampule assembly aligns with and presses against the seal 430, which seals a liquid communication path between the cannula and the ampule assembly.

A cap 450 is also provided for closing off the locking collar 426 when the vial coupler 410 is not in use. The cap 450 includes a body portion 452 which has a diameter greater than the outside diameter of the locking collar 426 and which is grasped by a user in order to place the cap 450 over the vial coupler. A threaded portion 452 is provided which comprises threads, preferably LUER-type threads for mating with threads 428 provided inside the locking collar 426. The cap 450 also includes a protrusion 456, similar in structure to the frusto-conical protrusion provided on both embodiments of the ampule assembly (12, 12' of FIGS. 1, 1a, 2 and 2a). The threaded portion 454 of the cap 450 is of a length sufficient so that when threaded into place, the protrusion 456 engages the seal 430 at the base of the locking collar 426, thus maintaining the locking collar 426 free from contamination.

Operation of the vial coupler will be described in connection with FIGS. 1a, 2a and 11. Operationally, an ampule assembly 2' is attached to the locking collar 426 of the vial coupler 410 which is connected, in turn, to a medication vial 411 by placing the shroud 414 of the vial coupler over the lid portion 420 of the vial. The cannula 424 pierces the self-sealing membrane 422 of the vial thereby allowing fluid communication between the contents of the medication vial and the orifice 14' of the ampule assembly 2'. The vial, coupler, and ampule assembly is then inverted so that liquid medication in the vial covers the point of the canula 424. The user forces the plunger handle 204 of the ampule assembly 2' forward, toward the orifice 14', thereby forcing air into the medication vial and causing a positive pressure therein. The user then moves the plunger handle 204 away from the orifice end 10' of the ampule assembly, producing a pressure differential or suction within the ampule chamber 6' that withdraws medication from the vial through the canula of the vial coupler and into the tubular chamber 6' of the ampule assembly 2'. Preferably, the ampule is filled with slightly more medication than is desired for an injection, so that any air in the ampule can be ejected by pushing the plunger back into the ampule chamber an appropriate distance, while the ampule is held in the vertical position, with the orifice up.

The user verifies that the correct dosage has been withdrawn into the ampule by viewing the plunger piston 8' in the ampule assembly 2' relative to the graduations 18' on the shell 4' as discussed previously with reference to FIG. 1a. The user then removes the ampule assembly from the vial coupler and stores the ampule assembly for later use, or connects the ampule assembly to the injector device to inject the selected dosage.

The foregoing descriptions of preferred embodiments of the needleless hypodermic jet injection system of this invention, which comprises the ampule assembly 2, 2', the handheld, spring actuated injector device 26, 26', a cocking/carrying case, and various liquid medication transfer devices, are given for illustrative purposes only. Because of variations which will be apparent to those skilled in the art, the present invention is not intended to be limited to the particular embodiments described above. The scope of the invention is defined in the following claims.

I claim:

1. A spring actuated needleless hypodermic jet injection system comprising:
    an ampule assembly comprising:
        a shell having a chamber for holding liquid medication between first and second ends of the shell;
        an orifice in the first end of the shell and communicating with the chamber through which liquid medication is drawn into and ejected out from the chamber; and
        a plunger assembly movable within the chamber for converting an applied force to a corresponding pressure applied to the liquid, the plunger assembly for drawing liquid medication into the chamber and for ejecting liquid medication out from the chamber;
    an injector for receiving and mounting the ampule assembly and for providing said applied force to move the plunger assembly, the injector comprising:
        a cylindrical housing having a front end, a back end, and defining a longitudinal channel therebetween, wherein the front end of the housing is open and configured to receive the second end of the ampule assembly;
        a piston mounted for sliding movement in the longitudinal channel, the piston for applying said force to the plunger assembly;
        a spring disposed within the channel and communicating with the piston, the spring for accumulating and storing a sufficient amount of energy when compressed to produce sufficient pressure to cause the liquid to leave the chamber via the orifice at such a velocity that it can be hypodermically injected at an injection site, wherein the energy is converted to said force by the piston when the spring is released;
        a trigger assembly coupled to the spring for manually releasing the stored energy;
        coupling means disposed in the open end of the injector housing for coupling the ampule assembly to the housing;
        a safety interlock assembly, coupled between the trigger assembly and the coupling means, the safety interlock operatively responsive to the ampule assembly as being coupled to the injector housing, the safety interlock assembly preventing release of the stored energy by the trigger assembly unless an ampule assembly is coupled to the injector; and
    a cocking/carrying case comprising a cavity, wherein the injector is disposed within the cavity, the cocking/carrying case comprising:
        a rectangular base and cover hingedly connected together at a short side such that the cover describes an arc when closed upon the base; and
        cocking means operatively responsive to the closing of the cover, for engaging the injector to compress the spring to accumulate said suitable amount of energy.

2. The injector system according to claim 1, wherein the cocking/carrying case further comprises a shuttle slidably mounted on the base, the shuttle including a centrally mounted and longitudinally extending ramrod configured to extend into the open front end of the injector housing when the injector is disposed in the cavity, the ramrod bearing against the injector piston such that when the lid is closed, the ramrod exerts a force on the piston to thereby compress the spring to accumulate said suitable amount of energy.

3. The injection system according to claim 2, wherein the cocking/carrying case further comprises thrust means connected between the cover and the shuttle, the thrust means translating the arcuate motion of the cover into a lateral motion of the shuttle.

4. A spring actuated needleless hypodermic jet injection system comprising:
    an ampule assembly comprising:
        a shell having a chamber for holding liquid medication between first and second ends of the shell;
        an orifice in the first end of the shell and communicating with the chamber through which liquid medication is drawn into and ejected out from the chamber; and a plunger assembly movable within the chamber for converting an applied force to a corresponding pressure applied to the liquid, the plunger assembly for drawing liquid medication into the chamber and for ejecting liquid medication out from the chamber;

an injector for receiving and mounting the ampule assembly and for providing said applied force to move the plunger assembly, the injector comprising:

a cylindrical housing having a front end, a back end, and defining a longitudinal channel therebetween, wherein the front end of the housing is open and configured to receive the second end of the ampule assembly;

a piston mounted for sliding movement in the longitudinal channel, the piston for applying said force to the plunger assembly;

a spring disposed within the channel and communicating with the piston, the spring for accumulating and storing a sufficient amount of energy when compressed to produce sufficient pressure to cause the liquid to leave the chamber via the orifice at such a velocity that it can be hypodermically injected at an injection site, wherein the energy is converted to said force by the piston when the spring is released;

a trigger assembly coupled to the spring for manually releasing the stored energy;

coupling means disposed in the open end of the injector housing for coupling the ampule assembly to the housing;

a safety interlock assembly, coupled between the trigger assembly and the coupling means, the safety interlock operatively responsive to the ampule assembly as being coupled to the injector housing, the safety interlock assembly preventing release of the stored energy by the trigger assembly unless an ampule assembly is coupled to the injector; and a cocking/carrying case having a base, a closable cover and a cavity, wherein the injector is disposed within the cavity, the cocking/carrying case including cocking means operatively responsive to the closing of the cover for engaging the injector to compress the spring to accumulate said suitable amount of energy, the cocking/carrying case further comprising a shuttle slidably mounted on the base, the shuttle including a centrally mounted and longitudinally extending ramrod configured to extend into the open front end of the injector housing when the injector is disposed in the cavity, the ramrod bearing against the injector piston such that when the lid is closed, the ramrod exerts a force on the piston to thereby compress the spring to accumulate said suitable amount of energy.

5. The injection system according to claim 4, wherein the cocking/carrying case further comprises thrust means connected between the cover and the shuttle, the thrust means translating an arcuate closing motion of the cover into a lateral motion of the shuttle.

6. A spring actuated needleless hypodermic jet injection system comprising:

an ampule assembly comprising:

a shell having a chamber for holding liquid medication between first and second ends of the shell;

an orifice in the first end of the shell and communicating with the chamber through which liquid medication is drawn into and ejected out from the chamber; and a plunger assembly movable within the chamber for converting an applied force to a corresponding pressure applied to the liquid, the plunger assembly for drawing liquid medication into the chamber and for ejecting liquid medication out from the chamber;

an injector for receiving and mounting the ampule assembly and for providing said applied force to move the plunger assembly, the injector comprising:

a cylindrical housing having a front end, a back end, and defining a longitudinal channel therebetween, wherein the front end of the housing is open and configured to receive the second end of the ampule assembly;

a piston mounted for sliding movement in the longitudinal channel, the piston for applying said force to the plunger assembly;

a spring disposed within the channel and communicating with the piston, the spring for accumulating and storing a sufficient amount of energy when compressed to produce sufficient pressure to cause the liquid to leave the chamber via the orifice at such a velocity that it can be hypodermically injected at an injection site, wherein the energy is converted to said force by the piston when the spring is released;

a trigger assembly coupled to the spring for manually releasing the stored energy;

coupling means disposed in the open end of the injector housing for coupling the ampule assembly to the housing;

a safety interlock assembly, coupled between the trigger assembly and the coupling means, the safety interlock operatively responsive to the ampule assembly as being coupled to the injector housing, the safety interlock assembly preventing release of the stored energy by the trigger assembly unless an ampule assembly is coupled to the injector;

a cocking/carrying case having a base, a closable cover and a cavity, wherein the injector is disposed within the cavity, the cocking/carrying case including cocking means operatively responsive to the closing of the cover for engaging the injector to compress the spring to accumulate said suitable amount of energy, wherein the cocking/carrying case further comprises a shuttle slidably mounted on the base, the shuttle including a centrally mounted and longitudinally extending ramrod configured to extend into the open front end of the injector housing when the injector is disposed in the cavity, the ramrod bearing against the injector piston such that when the lid is closed, the ramrod exerts a force on the piston to thereby compress the spring to accumulate said suitable amount of energy; and liquid transfer means for drawing liquid medication from a medication container into the ampule assembly through the orifice.

7. The injection system according to claim 6, wherein the cocking/carrying case further comprises thrust means connected between the cover and the shuttle, the thrust means translating an arcuate closing motion of the cover into a lateral motion of the shuttle.

\* \* \* \* \*